United States Patent [19]

Clonce et al.

[11] Patent Number: 4,480,116
[45] Date of Patent: Oct. 30, 1984

[54] PROCESS INHIBITOR FOR READILY POLYMERIZABLE ACRYLATE MONOMER

[75] Inventors: Ambrose J. Clonce; Michael Palmer, both of Kingsport; Samuel L. Gott, Mt. Carmel, all of Tenn.

[73] Assignee: Eastman Kodak Company, Rochester, N.Y.

[21] Appl. No.: 471,384

[22] Filed: Mar. 2, 1983

[51] Int. Cl.³ ............................ C07C 67/62; C07C 51/50
[52] U.S. Cl. ................................................. 560/4; 203/8; 203/62; 203/DIG. 21; 560/207; 560/215; 560/218; 562/522; 562/546; 562/598; 562/599; 562/600
[58] Field of Search ................. 560/4, 207, 215, 218; 562/522, 546, 598, 599, 600; 203/8, 62, DIG. 21

[56] References Cited

U.S. PATENT DOCUMENTS

| | | | |
|---|---|---|---|
| 2,255,483 | 9/1941 | D'Alelio | 560/4 |
| 2,758,135 | 8/1956 | Miller | 564/4 |
| 3,666,794 | 5/1972 | Otsuki et al. | 560/4 |
| 4,021,310 | 5/1977 | Shimizu et al. | 203/8 |

*Primary Examiner*—Natalie Trousof
*Assistant Examiner*—Vera C. Clarke
*Attorney, Agent, or Firm*—David E. Cotey; Daniel B. Reece, III

[57] ABSTRACT

The present invention provides an improvement in methods for preparing and processing readily polymerizable acrylate monomers. The improvement comprises employing phenyl-para-benzoquinone, 2,5-di-phenyl-para-benzoquinone, and mixtures thereof as process inhibitors. The process inhibitors are present in a concentration of about 50 to 3000 ppm, preferably about 250 to 2000 ppm, and most preferably about 500 ppm.

12 Claims, No Drawings

PROCESS INHIBITOR FOR READILY POLYMERIZABLE ACRYLATE MONOMER

BACKGROUND OF THE INVENTION

Readily polymerizable acrylate monomers are important chemicals of commerce. The current production of methyl methacrylate and related monomers is approximately 1.3 billion pounds per year. These monomers are most often prepared by methods involving a distillation step at elevated temperature and/or reduced pressure.

Acrylic acid and derivatives thereof are currently preferably prepared by the oxidation of propylene. The process involves a two-step oxidation, followed by an extraction, and vacuum distillation. Acrylic acid can also be produced by the reaction of acetylene, carbon monoxide, and water in the presence of nickel carbonyl. This method also involves the removal of product by distillation. A similar process which additionally includes methyl or ethyl alcohol as a reactant is employed for the preparation of methyl or ethyl acrylate, respectively. Again, distillation is employed to purify and collect the product.

A widely employed process for the preparation of methacrylic acid involves the acid hydrolysis of acetone cyanohydrin. Methyl methacrylate is prepared by a similar process involving the acid methanolysis of acetone cyanohydrin. Each of these methods likewise employs vacuum distillation at elevated temperatures (e.g., about 100° C.) in order to recover the product.

In the above-described processes for the preparation of acrylate monomers, like all other preparations of polymerizable monomers, care must be exercised to remove the products from the reaction mixture and to inhibit the monomer before uncontrolled polymerization can ensue. The reactivity of these acrylate monomers necessitates the use of a relatively large amount of process inhibitor in order to prevent polymerization. Currently used process inhibitors include hydroquinone, the methyl ether of hydroquinone, and p-benzoquinone. A compound which has been proposed for use as a process inhibitor is n-nitroso-phenylhydroxylamine. However, this compound is expensive and is reported to be extremely toxic.

When investigating the usefulness of a compound as a process inhibitor for acrylate monomer, a number of characteristics are evaluated. The compound must exhibit an effectiveness as a polymerization inhibitor equal to or greater than the currently employed or proposed process inhibitors. The compounds should exhibit a lower environmental impact and toxicity than currently employed and proposed process inhibitors. A process inhibitor which is proposed for use in acrylate monomer systems should be soluble in acrylate monomers, such as methyl methacrylate, or in suitable carrier solvents at levels which are high enough to allow the preparation of commercially useful stock solutions. Also, the process inhibitor must be a compound which does not entrain with the acrylate monomer during the final purification of the monomer.

It has now been found that all of these characteristics are surprisingly and unexpectedly exhibited by phenyl-para-benzoquinone, diphenyl-para-benzoquinone, and mixtures thereof.

Japanese Kokai Tokkyo Koho No. 81 86,123 discloses the use of 2-phenyl-1,4-benzoquinone as a polymerization inhibitor for aromatic vinyl compounds. The use of 2,5-diphenyl-p-benzoquinone as a polymerization inhibitor for a polyester resin system diluted with styrene is disclosed in Proceedings of the 23rd Annual Technical Conference of the Reinforced Plastics/Composites Division of the Society of the Plastics Industry (Plastics Ind., Inc.: New York) 1968. The use of diphenyl-p-benzoquinone in admixture with another inhibitor to inhibit the crosslinking of polyolefins is disclosed in British Patent Specification No. 1,077,634. The use of diphenyl-p-benzoquinone as an inhibitor in the curing of unsaturated polyester is disclosed in U.S. Pat. No. 3,026,286. None of these prior art references recognizes the unique characteristics of phenyl-para-benzoquinone and/or diphenyl-para-benzoquinone which make these compounds, either alone or in mixtures, desirable as process inhibitors for acrylate monomers.

SUMMARY OF THE INVENTION

The present invention provides an improvement in processes for the preparation of readily polymerizable acrylate monomers. The improvement comprises employing a process inhibitor comprising phenyl-para-benzoquinone, 2,5-diphenyl-para-benzoquinone, or a mixture thereof.

DETAILED DESCRIPTION OF THE INVENTION

The present invention relates to the use of phenyl-para-benzoquinone, 2,5-diphenyl-para-benzoquinone, or a mixture thereof as a process inhibitor in the preparation of readily polymerizable acrylate monomers. As used herein, the term "process inhibitor" refers to a polymerization inhibitor which is employed during the preparation and processing of the monomer. Process inhibitors can be distinguished from product inhibitors, which are combined with the monomer in order to inhibit polymerization during storage and handling.

According to the process of the present invention, phenyl-para-benzoquinone, 2,5-diphenyl-para-benzoquinone, or a mixture thereof is employed as a process inhibitor during the preparation and processing of certain monomeric substances. These benzoquinone derivatives are well known chemical compounds whose preparation is well known in the art. Phenyl-para-benzoquinone and diphenyl-para-benzoquinone are available commercially from a number of sources.

While phenyl-para-benzoquinone appears to be more effective as a process inhibitor, and is therefore preferred for use in the process of the present invention, either of the above-identified compounds or mixtures thereof may be used in the process of the present invention. Furthermore, additional inhibitors may also be used in combination with the above-identified compounds. These additional inhibitors may be other known process inhibitors or may be product inhibitors. Such additional inhibitors may include para-benzoquinone, hydroquinone, tert-butyl catechol, diphenylamine, the methyl ether of hydroquinone, etc.

The present process is applicable to readily polymerizable acrylate monomers. The term "acrylate monomer" is intended to include acrylic acid, methacrylic acid, and the many various esters thereof. While the following is not intended to be an exhaustive listing of such compounds, the esters of acrylic acid can include n-alkyl esters, such as methyl acrylate, ethyl acrylate, propyl acrylate, butyl acrylate, pentyl acrylate, hexyl acrylate, heptyl acrylate, octyl acrylate, decyl acrylate, dodecyl acrylate, hexadecyl acrylate, etc.; secondary and branched-chain alkyl esters, such as isopropyl acrylate, isobutyl acrylate, sec-butyl acrylate, 2-methylbutyl acrylate, 3-methylbutyl acrylate, 2-ethylbutyl acrylate, 1,3-dimethylbutyl acrylate, 2-ethylhexyl acrylate, 1-methylheptyl acrylate, etc.; esters of olefinic alcohols, such as allyl acrylate, 2-methylallyl acrylate, 2-butenyl acrylate, 3,7-dimethyl-2,6-octadienyl acrylate, furfuryl acrylate, etc.; amino alkyl esters, such as 2-(dimethylamino)ethyl acrylate, 2-(diethylamino)ethyl acrylate, 2-(dibutylamino)ethyl acrylate, 2-morpholinoethyl acrylate, etc.; esters of ether alcohols, such as 2-methoxyethyl acrylate, 2-ethoxyethyl acrylate, 2-isopropoxyethyl acrylate, 2-butoxyethyl acrylate, 2-(2-ethylhexoxy)ethyl acrylate, 2-phenoxyethyl acrylate, 2-benzyloxyethyl acrylate, 2-(2-methoxyethoxy)ethyl acrylate, 2-(2-ethoxyethoxy)-ethyl acrylate, 2-(2-phenoxyethoxy)ethyl acrylate, tetrahydrofurfuryl acrylate, etc.; cycloalkyl esters, such as cyclohexyl acrylate, 2-methylcyclohexyl acrylate, 3,3,5-trimethylcyclohexyl acrylate, 4-cyclohexylcyclohexyl acrylate, etc.; esters of halogenated alcohols such as 2-bromoethyl acrylate, 2-chloroethyl acrylate, 3-bromopropyl acrylate, 2,3-dibromopropyl acrylate, 1-bromoisopropyl acrylate, 3-chloropropyl acrylate, 1,3-dichloroisopropyl acrylate, etc.; nitroalkyl esters, such as 2-nitroethyl acrylate, 2-nitropropyl acrylate, 2-nitrobutyl acrylate, 2-methyl-2-nitropropyl acrylate, 2,2-dinitropropyl acrylate, etc.; glycol diacrylates, such as ethylene glycol diacrylate, propylene glycol diacrylate, 1,3-propanediol diacrylate, 1,4-butanediol diacrylate, diethylene glycol diacrylate, triethylene glycol diacrylate, dipropylene glycol diacrylate, 2,5-hexanediol diacrylate, 2,2-diethyl-1,3-propanediol diacrylate, etc.

The esters of methacrylic acid similarly are legion. Examples of such esters include methyl methacrylate, ethyl methacrylate, propyl methacrylate, isopropyl methacrylate, butyl methacrylate, isobutyl methacrylate, sec-butyl methacrylate, tert-butyl methacrylate, hexyl methacrylate, octyl methacrylate, isooctyl methacrylate, 2-ethylhexyl methacrylate, decyl methacrylate, vinyl methacrylate, allyl methacrylate, oleyl methacrylate, cyclohexyl methacrylate, 1-methylcyclohexyl methacrylate, 3,3,5-trimethylcyclohexyl methacrylate, phenyl methacrylate, benzyl methacrylate, 1,2-propanediol dimethacrylate, 1,3-butanediol dimethacrylate, 1,4-butanediol dimethacrylate, 2,5-dimethyl-1,6-hexanediol dimethacrylate, glycidyl methacrylate, 2,3-epoxybutyl methacrylate, 2-hydroxyethyl methacrylate, methoxymethyl methacrylate, ethoxymethyl methacrylate, 2-ethoxyethoxymethyl methacrylate, benzyloxymethyl methacrylate, 1-ethoxyethyl methacrylate, tetrahydrofuryl methacrylate, dimethylaminoethyl methacrylate, diethylaminoethyl methacrylate, tert-butylaminoethyl methacrylate, 3-diethylaminopropyl methacrylate, cyanomethyl methacrylate, 4-thiocyanatobutyl methacrylate, 2-ethylenephosphitopropyl methacrylate, dimethylphosphinomethyl methacrylate, 2-cyanoethyl methacrylate, chloromethyl methacrylate, 1,3-dichloro-2-propyl methacrylate, 4-bromophenyl methacrylate, 2-bromoethyl methacrylate, 2,3-dibromopropyl methacrylate, 2-iodoethyl methacrylate, etc.

Acrylate monomers which are preferred for use in the process of the present invention include acrylic acid, acrylic acid esters having 1–8 carbon atoms in the alcohol moiety thereof, methacrylic acid, methacrylic acid esters having 1–8 carbon atoms in the alcohol moiety thereof, and mixtures of the foregoing. Such compounds are represented by formula I below, wherein R represents hydrogen or methyl and R' represents hydrogen or an alcohol derivative having 1–8 carbon atoms.

$$H_2C=\underset{\underset{R}{|}}{C}-\underset{\underset{}{}}{\overset{\overset{O}{\|}}{C}}-O-R' \qquad (I)$$

Acrylate monomers represented by Formula I above which are especially preferred for use in the process of the present invention include acrylic acid, methyl acrylate, ethyl acrylate, butyl acrylate, 2-ethylhexyl acrylate, methacrylic acid, methyl methacrylate, ethyl methacrylate, butyl methacrylate, 2-ethylhexyl methacrylate, and mixtures of the foregoing. The acrylate monomer which is most preferred for use in the process of the present invention is methyl methacrylate. While portions of the present specification may refer specifically to methyl methacrylate as an illustrative member of this class of compounds, it is to be understood that this specification applies to all members of the described class of readily polymerizable acrylate monomers.

As stated above, during the latter stages of current processes for the production of acrylate monomers, the crude monomer is typically subjected to distillation (usually at elevated temperatures and/or reduced pressures) in order to remove excess reactants and other impurities from the desired product. In accordance with the process of the present invention, phenyl-para-benzoquinone, diphenyl-para-benzoquinone, and mixtures thereof are employed as process inhibitors during the preparation of the monomer and especially during the distillation step, which is when polymerization is most likely to occur.

The process inhibitor can be supplied to the process in a variety of ways. Preferably, a separate inhibitor stream is provided directly to each reaction vessel and/or distillation column in which polymerization is likely to occur. For example, in the production of methyl methacrylate by the acetone cyanohydrin process, acetone cyanohydrin and concentrated sulfuric acids are pumped into a cooled hydrolysis kettle to form the intermediate methacrylamide sulfate. The stream leaving the hydrolysis kettle is dehydrated and cooled, after which it goes into an esterification kettle where it is reacted continuously with methanol. An inhibitor is advantageously added to this esterification kettle, and also to the subsequent acid stripping column and rectifier column. Regardless of the manner in which the process inhibitor is provided to the reaction system, the inhibitor is typically removed from the system in the final distillation wherein crude monomer is taken overhead and the remaining impurities and the process inhibitor are taken off as bottoms from the column. Alternative and/or additional locations for the introduction of process inhibitor and adaptations to systems for the production of other acrylate monomers will be apparent to the person of ordinary skill in the art.

The process inhibitor is provided to the reaction system in an amount which is sufficient to effect the inhibition of polymerization. Typically, the process inhibitor will be present in an amount of about 50 to 3,000 ppm, based upon the weight of process inhibitor per total weight of reactants and products present in the reaction system. Preferably, the process inhibitor is present in a concentration of about 250 to 2,000 ppm, with a concentration of about 500 to 1,000 (e.g., about 500) ppm being especially preferred.

The process inhibitor can be provided to the acrylate monomer preparation process either directly or as a stock solution. Phenyl-para-benzoquinone, diphenyl-para-benzoquinone, and mixtures thereof are sufficiently soluble in suitable carrier solvents to allow the preparation of such a stock solution. Suitable carrier solvents include lower aliphatic alcohols, water, and, preferably, methyl methacrylate itself. In the preferred embodiment wherein methyl methacrylate is employed as the carrier solvent, the stock solution commonly comprises about 5 to 10% by weight of inhibitor in the solution. The use of stock solutions of process inhibitors is well known in the art and is a wide-spread practice.

The invention will be further illustrated by the following example although it will be understood that this example is included merely for purposes of illustration and is not intended to limit the scope of the invention.

EXAMPLE

This example illustrates the improved inhibiting effect provided by phenyl-para-benzoquinone and 2,5-diphenyl-para-benzoquinone.

In each run of the present example, the indicated process inhibitor was provided in a concentration of 500 ppm to methyl methacrylate monomer which had been distilled to remove storage inhibitor.

The inhibitors which were employed were phenyl-para-benzoquinone, available commercially from Eastman Kodak Organic Chemicals; 2,5-diphenyl-p-benzoquinone, available commercially from Eastman Kodak Organic Chemicals; p-benzoquinone, available commercially from Eastman Chemical Products, Inc.; and n-nitroso-phenyl-hydroxylamine, available commercially from Mallinckrodt.

The inhibited methyl methacrylate was refluxed at 98° C. for the indicated periods of time. At the end of each of the indicated periods of time, one milliliter of solution was removed, weighed, and contacted with methanol. Any polymer present in the solution sample was allowed to precipitate over a period of time of one hour. The solution was then centrifuged and filtered so as to remove any precipitated polymer. The precipitated polymer was dried and weighed. The results are given in Table I. In Table I, a Percent Polymer Formation of 0.00 indicates that a clear solution with no signs of polymer formation was obtained; a Percent Polymer Formation of <0.02 signifies that a hazy solution was obtained, but that the Percent Polymer Formation was too low for detection (i.e., <0.02%).

TABLE I

| Inhibitor | Percent Polymer Formation (Hours Refluxed) | | | | | |
|---|---|---|---|---|---|---|
| | 2 | 4 | 8 | 24 | 32 | 48 |
| Phenyl-p-Benzoquinone | 0.00 | <0.02 | 0.02 | 0.11 | 0.19 | 0.24 |
| 2,5-Diphenyl-p-Benzoquinone | <0.02 | 0.04 | 0.09 | 0.32 | 0.33 | — |
| p-Benzoquinone | 0.20 | 0.25 | 0.35 | 1.2 | 1.3 | — |
| n-Nitroso-Phenyl-hydroxyl Amine | 0.00 | 0.00 | 0.00 | 0.33 | 0.50 | 1.3 |

The results of Table I indicate the superior effectiveness of phenyl-para-benzoquinone and 2,5-diphenyl-para-benzoquinone as process inhibitors for acrylate monomers, such as methyl methacrylate. The samples in which phenyl-para-benzoquinone was employed as a process inhibitor showed little, if any, polymer formation through eight hours of reflux. From eight hours to 48 hours, only minimal amounts of polymer were formed. Likewise, 2,5-diphenyl-p-benzoquinone showed minimal polymer formation through 32 hours of reflux. In contrast, a currently employed process inhibitor, p-benzoquinone, showed significant polymer formation even after two hours of reflux with a sharp increase in polymer formation observed at relatively longer reflux times. Also in contrast to the process inhibitors of the present invention, n-nitroso-phenyl-hydroxylamine, a proposed commercial inhibitor, demonstrated undesirable levels of polymer formation at 32 to 48 hours of reflux.

Thus, the process inhibitors of the present invention demonstrate an advantageous effectiveness as polymerization inhibitors. In addition, the process inhibitors employed in the process of the present invention demonstrate significantly reduced environmental and toxic effects when compared to the proposed commercial inhibitor n-nitroso-phenyl-hydroxylamine.

The process inhibitors of the present invention are therefore far more safe and effective than current commercially employed or proposed acrylate monomer process inhibitors.

The invention has been described in detail with particular reference to preferred embodiments thereof, but it will be understood that variations and modifications can be effected within the spirit and scope of the invention.

We claim:

1. In a process for the preparation of readily polymerizable acrylate monomer which includes a distillation step at elevated temperature and/or reduced pressure, the improvement which comprises providing a process polymerization inhibitor comprising phenyl-para-benzoquinone, 2,5-diphenyl-para-benzoquinone, or a mixture thereof, said process polymerization inhibitor being present in a concentration of about 50 to 3000 ppm.

2. The process of claim 1 wherein said process polymerization inhibitor comprises phenyl-para-benzoquinone.

3. The process of claim 1 wherein said process polymerization inhibitor is present in a concentration of about 250 to 2000 ppm.

4. The process of claim 1 wherein said process polymerization inhibitor is present in a concentration of about 500 ppm.

5. The process of claim 1 wherein said acrylate monomer comprises acrylic acid, acrylic acid esters having 1 to 8 carbon atoms in the alcohol moiety thereof, methacrylic acid, methacrylic acid esters having 1 to 8 carbon atoms in the alcohol moiety thereof, or a mixture of the foregoing.

6. The process of claim 5 wherein said acrylate monomer comprises acrylic acid, methyl acrylate, ethyl acrylate, butyl acrylate, 2-ethylhexyl acrylate, methacrylic acid, methyl methacrylate, ethyl methacrylate, butyl methacrylate, 2-ethylhexyl methacrylate, or a mixture of the foregoing.

7. The process of claim 6 wherein said acrylate monomer comprises methyl methacrylate.

8. In a process for the preparation of readily polymerizable acrylate monomer comprising acrylic acid, acrylic acid esters having 1 to 8 carbon atoms in the alcohol moiety thereof, methacrylic acid, methacrylic acid esters having 1 to 8 carbon atoms in the alcohol moiety thereof, or a mixture of the foregoing, said process comprising a distillation step at elevated temperature and/or reduced pressure, the improvement which comprises providing a process polymerization inhibitor comprising phenyl-para-benzoquinone, 2,5-diphenyl-para-benzoquinone, or a mixture thereof, said process polymerization inhibitor being present in a concentration of about 250 to 2000 ppm.

9. The process of claim 8 wherein said process polymerization inhibitor comprises phenyl-para-benzoquinone.

10. The process of claim 8 wherein said process polymerization inhibitor is present in a concentration of about 500 ppm.

11. The process of claim 8 wherein said acrylate monomer comprises acrylic acid, methyl acrylate, ethyl acrylate, butyl acrylate, 2-ethylhexyl acrylate, methacrylic acid, methyl methacrylate, ethyl methacrylate, butyl methacrylate, 2-ethylhexyl methacrylate, or a mixture of the foregoing.

12. The process of claim 11 wherein said acrylate monomer comprises methyl methacrylate.

* * * * *